（12） United States Patent
McKay

(10) Patent No.: US 8,715,223 B2
(45) Date of Patent: May 6, 2014

(54) DEVICE AND METHOD FOR DELIVERY OF A DRUG DEPOT NEAR THE NERVE

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 825 days.

(21) Appl. No.: 12/507,197

(22) Filed: Jul. 22, 2009

(65) Prior Publication Data

US 2011/0022028 A1 Jan. 27, 2011

(51) Int. Cl.
*A61M 31/00* (2006.01)

(52) U.S. Cl.
USPC .................................. 604/57; 604/59

(58) Field of Classification Search
USPC .................................. 604/57, 16, 59
See application file for complete search history.

(56) References Cited

U.S. PATENT DOCUMENTS

| | | | |
|---|---|---|---|
| 5,131,401 A | 7/1992 | Westenskow et al. | |
| 5,196,015 A | 3/1993 | Neubardt | |
| 5,391,081 A | 2/1995 | Lampotang et al. | |
| 5,466,219 A | 11/1995 | Lynn et al. | |
| 5,474,558 A | 12/1995 | Neubardt | |
| 5,928,158 A | 7/1999 | Aristides | |
| 6,273,877 B1 | 8/2001 | West et al. | |
| 6,298,256 B1 | 10/2001 | Meyer | |
| 6,554,778 B1 | 4/2003 | Fleming, III | |
| 6,565,541 B2 | 5/2003 | Sharp | |
| 6,582,441 B1 * | 6/2003 | He et al. | 606/129 |
| 7,070,583 B1 | 7/2006 | Higuchi et al. | |
| 7,081,123 B2 | 7/2006 | Merboth et al. | |
| 7,212,865 B2 | 5/2007 | Cory | |
| 7,215,425 B2 | 5/2007 | Rezachek et al. | |
| 7,400,930 B2 | 7/2008 | Sharkey et al. | |
| 2003/0045808 A1 | 3/2003 | Kaula et al. | |
| 2004/0228901 A1 | 11/2004 | Trieu et al. | |
| 2007/0118142 A1 | 5/2007 | Krueger et al. | |
| 2007/0255281 A1 | 11/2007 | Simonton et al. | |
| 2007/0255282 A1 | 11/2007 | Simonton et al. | |
| 2007/0260184 A1 | 11/2007 | Justis et al. | |
| 2007/0260201 A1 | 11/2007 | Prausnitz et al. | |
| 2007/0265582 A1 | 11/2007 | Kaplan et al. | |
| 2008/0004570 A1 | 1/2008 | Simonton et al. | |
| 2008/0004703 A1 | 1/2008 | Trieu et al. | |
| 2008/0102097 A1 | 5/2008 | Zanella | |
| 2008/0125637 A1 * | 5/2008 | Geist et al. | 600/372 |
| 2008/0139877 A1 | 6/2008 | Chu et al. | |

FOREIGN PATENT DOCUMENTS

| | | |
|---|---|---|
| DE | 19640670 A1 | 5/1998 |
| EP | 1625870 A2 | 2/2006 |
| WO | 0038574 A1 | 7/2000 |
| WO | 2008091777 A2 | 7/2008 |

OTHER PUBLICATIONS

International Search Report and Written Opinion for US Application PCT/US2010/030699, the PCT counterpart of the present application mailed on Dec. 23, 2010.

\* cited by examiner

*Primary Examiner* — Kevin C Sirmons
*Assistant Examiner* — Deanna K Hall

(57) ABSTRACT

Drug depot delivery devices and methods are provided for delivering one or more drug depots in close proximity to the nerve of a patient with or without repositioning the cannula. The device includes an electronic monitor for detecting the proximity of the tip of the cannula to a nerve. In some embodiments, a method of delivering a drug depot is provided by detecting the nerve and delivering the drug depot near the nerve.

20 Claims, 8 Drawing Sheets

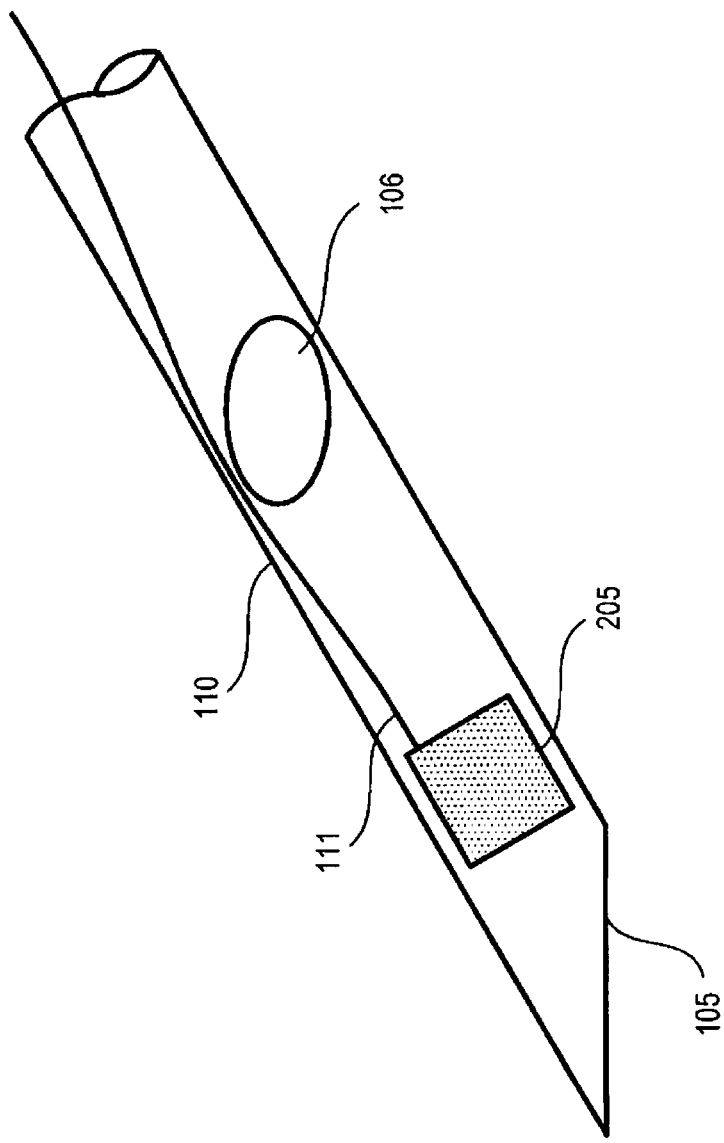

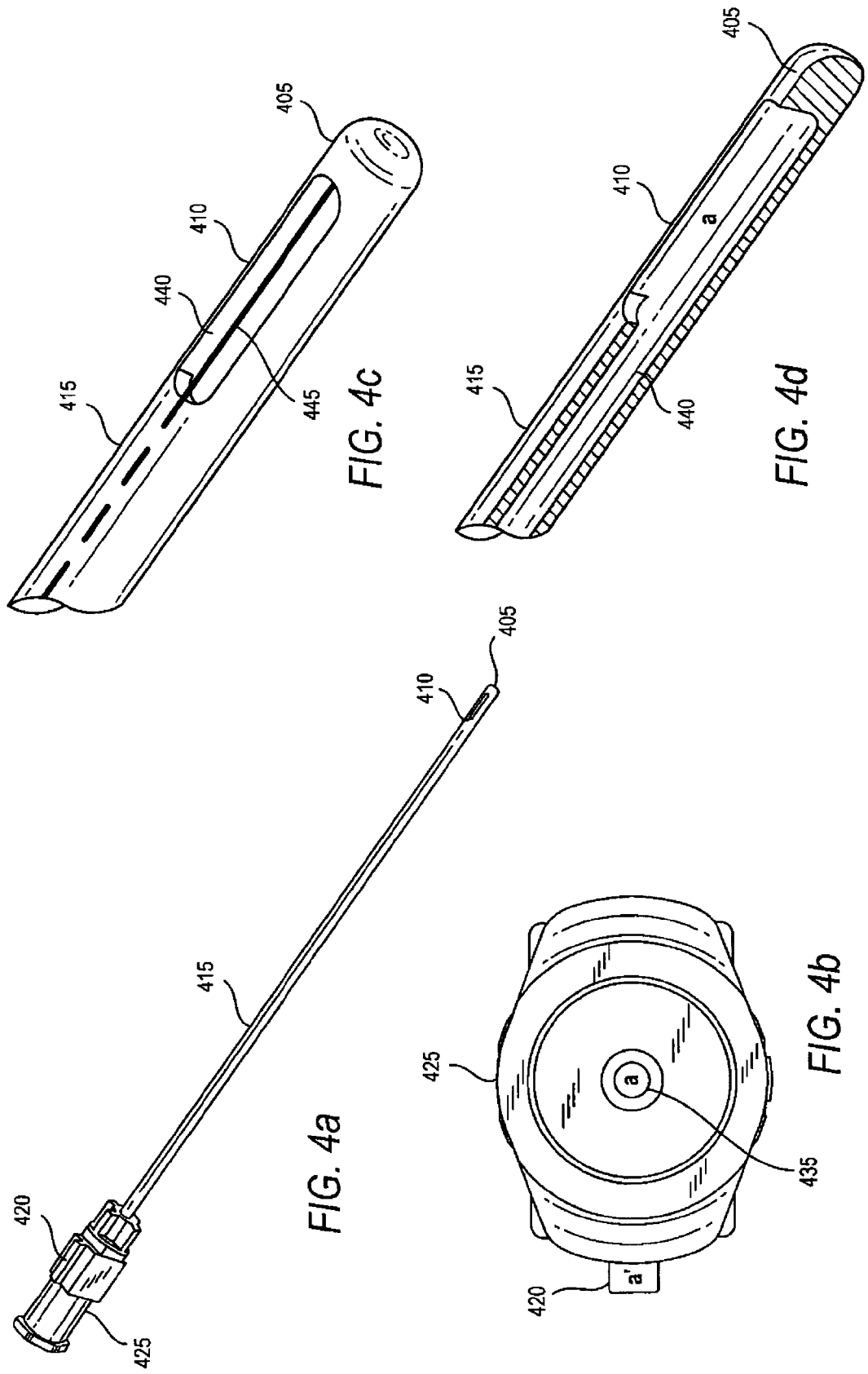

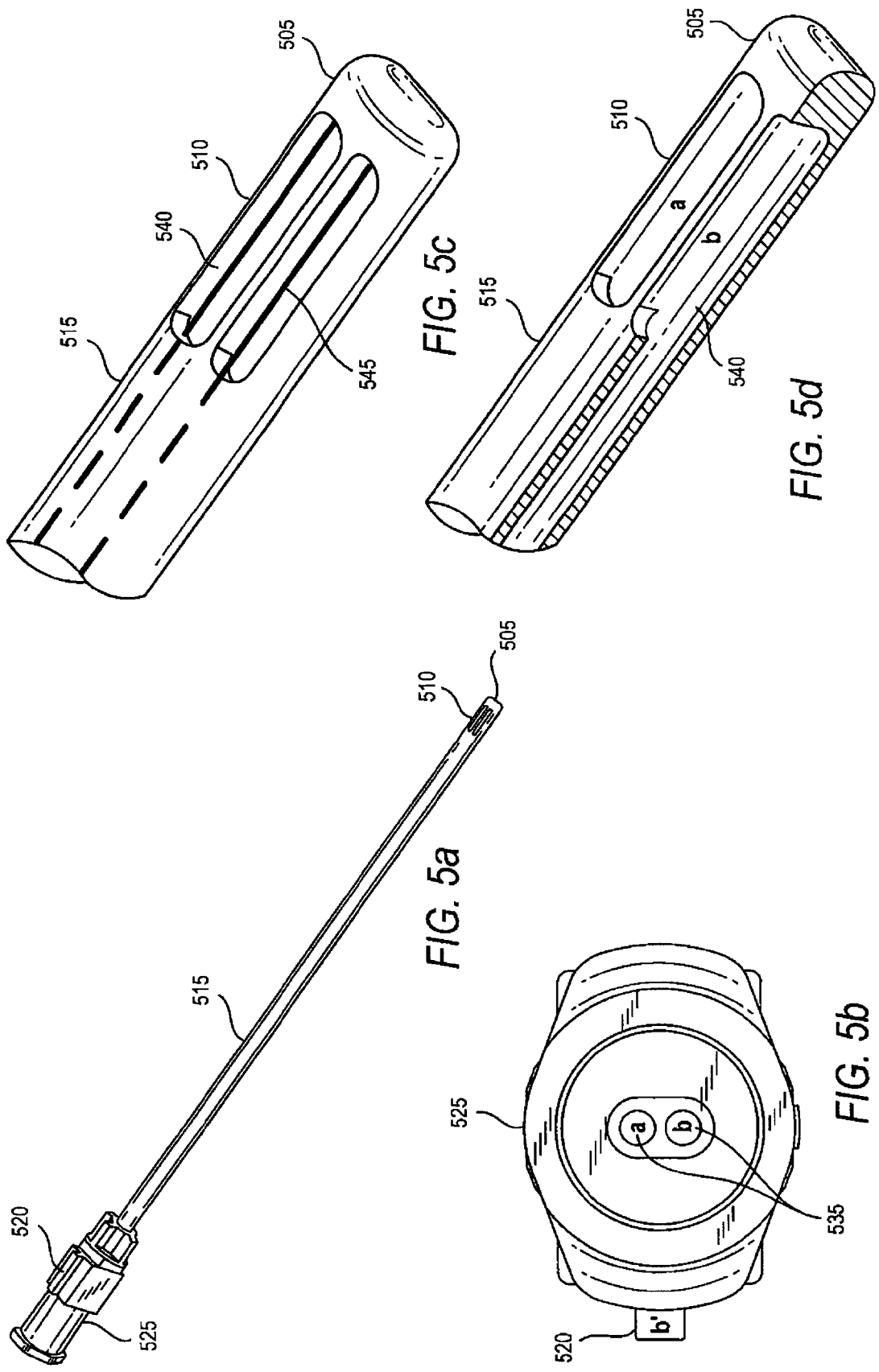

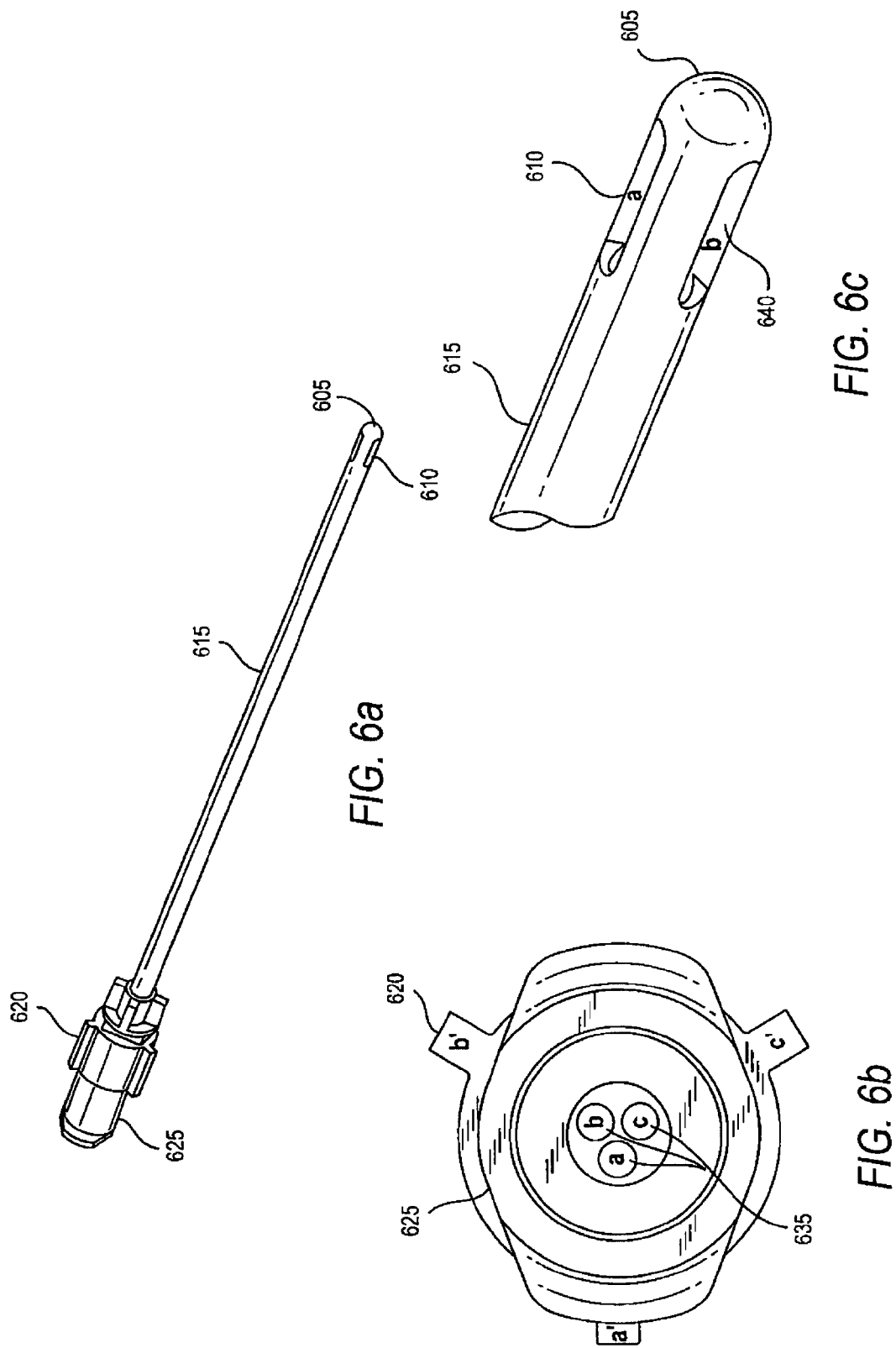

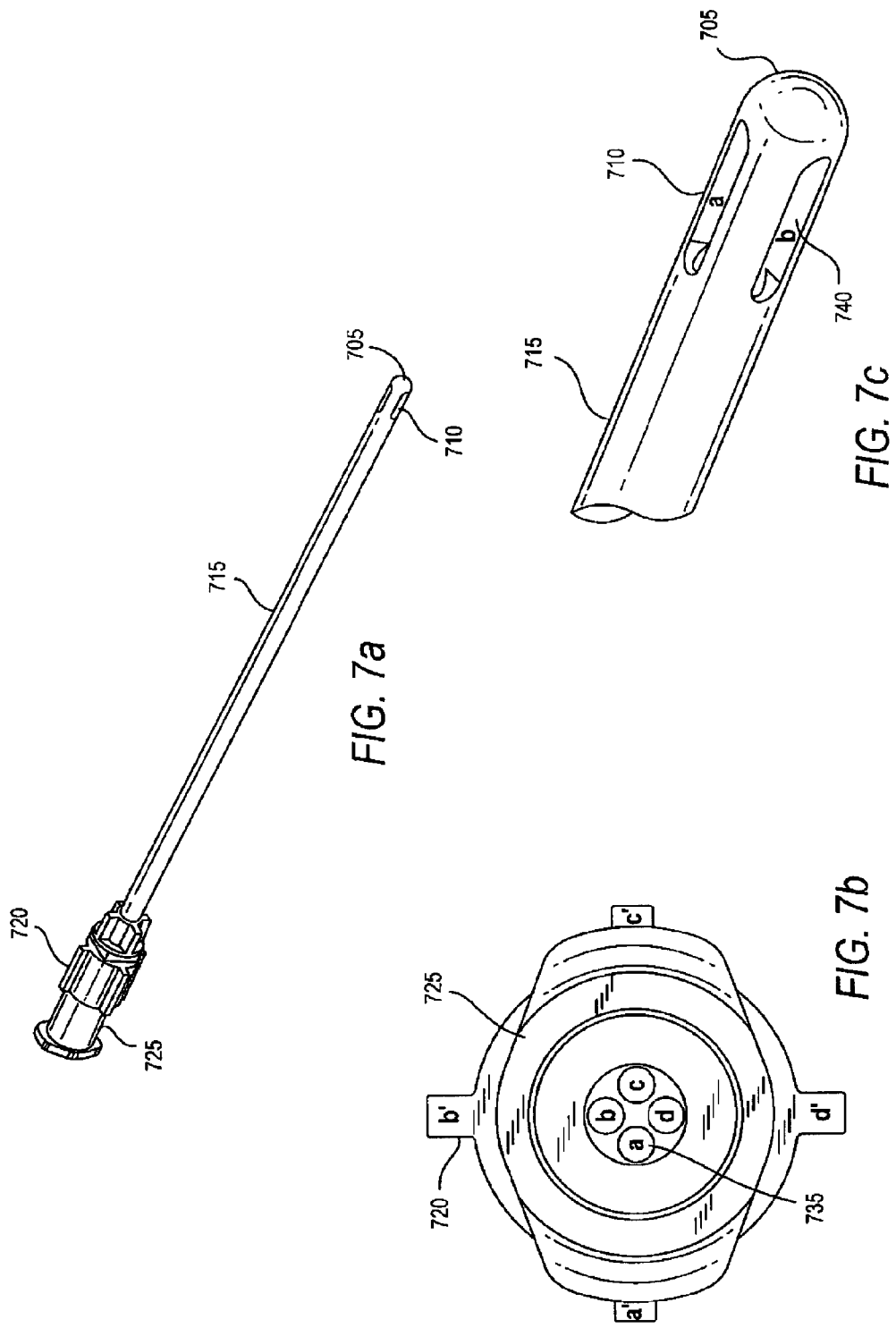

DEVICE AND METHOD FOR DELIVERY OF A DRUG DEPOT NEAR THE NERVE

BACKGROUND

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Recently, drug depots have been developed which allow a drug to be introduced or administered to sites beneath the skin of a patient so that the drug is slowly released over a long period of time. Such drug depots allow the drug to be released from the depot in a relatively uniform dose over weeks, months or even years. This method of administering drugs is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain, and pain associated with injury or repair of cervical, thoracic, and/or lumbar vertebrae or intervertebral discs, rotator cuff, articular joint, TMJ, tendons, ligaments, muscles, and the like.

Sometimes the drug depot may be delivered using imagining procedures, such as for example, ultrasound, fluoroscopy, x-ray, etc. Unfortunately, these imaging procedures often do not allow the clinician to detect nerve tissue. Therefore, when the drug depot is implanted at the target tissue site, the nerve tissue is not detected by the imaging procedure so the drug depot will either be implanted at a distance far away from the nerve decreasing efficacy of the drug depot or the nerve may be damaged during drug delivery. Nerve damage from drug delivery may range in severity from mildly annoying to severe disabling nerve problems, such as paralysis.

Therefore, new drug depot methods and devices are needed, which can easily allow accurate and precise implantation of a drug depot near the nerve of the patient causing minimal physical and psychological trauma to the patient. By implanting the drug depot near or in close proximity to the nerve, the drug depot efficacy is improved and the risk of nerve damage from procedure to implant the drug depot is reduced.

SUMMARY

New drug depot methods and devices are provided which can easily allow accurate and precise implantation of a drug depot near the nerve of the patient thus improving the efficacy of the drug depot. In some embodiments, new drug depot methods and devices are provided that allow nerve detection and implantation of the drug depot in close proximity to the nerve while reducing the risk of damaging the nerve on implantation. In some embodiments, a device and method is provided comprising at least one nerve detection cannula that detects the nerve and at least one drug delivery cannula to deliver the drug depot near the nerve. In some embodiments, at least one cannula and method is provided that both detects the nerve and delivers the drug depot near the nerve.

In one embodiment, a method of delivering a drug depot to a delivery site near a nerve of a patient is provided, the method comprising: detecting the nerve of the patient; and positioning near the nerve of the patient a cannula having a proximal end and a distal end, the proximal end of the cannula having an opening to receive the drug depot, the distal end of the cannula having an opening for passage of the drug depot from the distal end of the cannula to the delivery site near the nerve of the patient; and delivering the drug depot at the delivery site near the nerve by sliding a plunger having a handle and a tip adapted for dispensing the drug depot, wherein the tip of the plunger is slidably receivable within the cannula to deliver the drug depot out the opening of the cannula to the delivery site near the nerve of the patient.

In another embodiment, a method of delivering a drug depot to a delivery site near a nerve of a patient is provided, the method comprising: positioning a first cannula having a nerve sensing unit comprising an electrical contact and an alarm coupled to the nerve sensing unit, wherein when the cannula contacts the nerve or is in close proximity to the nerve, the alarm is activated to indicate a location of the nerve; positioning near the nerve of the patient a second cannula having a proximal end and a distal end, the proximal end of the second cannula having an opening to receive the drug depot, the distal end of the second cannula having an opening for passage of the drug depot from the distal end of the second cannula to the delivery site near the nerve of the patient; and delivering the drug depot at the delivery site near the nerve by sliding a plunger having a handle and a tip adapted for dispensing the drug depot, wherein the tip of the plunger is slidably receivable within the second cannula to deliver the drug depot out the opening of the second cannula to the delivery site near the nerve of the patient.

In yet another embodiment, a device is provided for delivering a drug depot at or near a nerve site beneath the skin of a patient, the device comprising: a cannula having a proximal end and a distal end, the proximal end of the cannula having an opening to receive the drug depot, the distal end of the cannula capable of insertion at or near the nerve site beneath the skin of the patient and having an opening for passage of the drug depot; a plunger being slidably receivable within the opening of the proximal end of the cannula, the plunger having a first end and a tip at a second end, the first end being capable of moving the tip of the plunger to an extended position; a nerve sensing unit disposed on or within the device, the nerve sensing unit comprising an electrical contact material configured to receive electrical impulses from the nerve site so as to detect the nerve.

In one exemplary embodiment, a device is provided for delivering a drug depot to a delivery site near a nerve of a patient, the device comprising: a first cannula having a nerve sensing unit comprising an electrical contact and an alarm coupled to the nerve sensing unit, wherein when the cannula contacts the nerve or is in close proximity to the nerve, the alarm is activated to indicate a location of the nerve; a second cannula having a proximal end and a distal end, the proximal end of the second cannula having an opening to receive the drug depot, the distal end of the second cannula having an opening for passage of the drug depot from the distal end of the second cannula to the delivery site near the nerve of the patient; and a plunger having a handle and a tip adapted for dispensing the drug depot, wherein the tip of the plunger is slidably receivable within the second cannula to deliver the drug depot out the opening of the second cannula to the delivery site near the nerve of the patient.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 2a illustrates an exemplary embodiment of an "all in one" device having a cannula with a side port at the distal end of the cannula near the tip and a sensor to detect proximity to a nerve. The nerve is detected before the drug depot is implanted next to the nerve.

FIG. 4a illustrates an exemplary embodiment of a drug delivery cannula for the drug delivery device having a single side port and a blunt tip at the distal end of the cannula for delivering a drug depot to a delivery site.

FIG. 4b illustrates an exemplary embodiment of the top view of the proximal end of a drug delivery cannula having a single opening or chamber for depositing a drug depot for delivery through the cannula to a delivery site, the opening also configured to receive a plunger to facilitate the delivery of the drug depot.

FIG. 4c illustrates an exemplary embodiment of the distal end of a drug delivery cannula having a single side port for delivering a drug depot at a delivery site.

FIG. 4d illustrates an exemplary embodiment of the cross-section view of a drug delivery cannula having a single inner chamber for delivering a drug depot through a single side port.

FIG. 5a illustrates an exemplary embodiment of a cannula of a drug delivery device having a double port at the distal end of the cannula for delivering multiple drug depots to a delivery site.

FIG. 5b illustrates an exemplary embodiment of the top view of the proximal end of a cannula having a double opening or chamber for depositing multiple drug depots for delivery through the cannula to a delivery site, the opening also configured to receive a plunger configured to facilitate the delivery of the drug depots.

FIG. 5c illustrates an exemplary embodiment of the distal end of a cannula having a double side port for delivering multiple drug depots at a delivery site.

FIG. 5d illustrates an exemplary embodiment of the cross-section view of a cannula having two inner chambers for delivering multiple drug depots through a two side port opening.

FIG. 6a illustrates an exemplary embodiment of a cannula of a drug delivery device having a triple side port opening at the distal end of the cannula and a blunt tip for delivering multiple drug depots to a delivery site.

FIG. 6b illustrates an exemplary embodiment of the top view of the proximal end of a cannula having a triple opening for depositing multiple drug depots for delivery through the cannula to a delivery site, the opening also configured to receive a plunger configured to facilitate the delivery of the drug depots.

FIG. 6c illustrates an exemplary embodiment of the distal end of a cannula having a triple side port opening for delivering multiple drug depots at a delivery site.

FIG. 7a illustrates an exemplary embodiment of a cannula of a drug delivery device having a quadruple side port opening and a blunt tip at the distal end of the cannula for delivering multiple drug depots to a delivery site.

FIG. 7b illustrates an exemplary embodiment of the top view of the proximal end of a cannula having a quadruple side port opening for depositing multiple drug depots for delivery through the cannula to a delivery site, the opening also configured to receive a plunger configured to facilitate the delivery of the drug depots.

FIG. 7c illustrates an exemplary embodiment of the distal end of a cannula having a quadruple side port opening for delivering multiple drug depots at a delivery site. The distal end of the cannula has a blunt tip.

Figure 1:
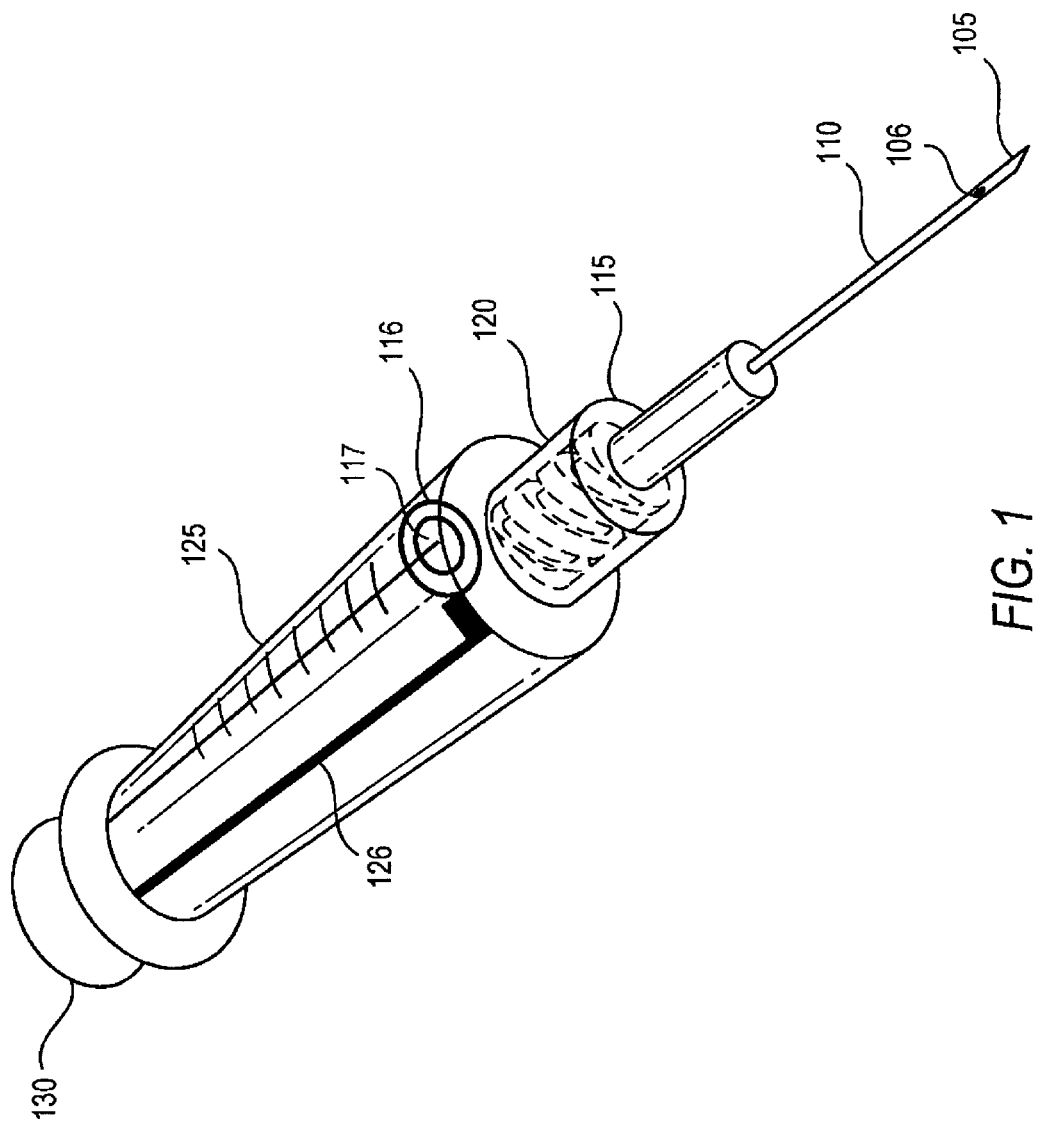
FIG. 1 illustrates an exemplary embodiment of an "all in one" cannula drug delivery device having a cannula, a housing, a sensor to detect the nerve, and a plunger for delivering the drug depot to a delivery site. This "all in one" device allows the nerve to be detected before the drug depot is implanted next to the nerve.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1, and a maximum value, of equal to, or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New drug depot methods and devices are provided which can easily allow accurate and precise implantation of a drug depot near the nerve of the patient thus improving the efficacy of the drug depot. In some embodiments, new drug depot methods and devices are provided that allow nerve detection and implantation of the drug depot in close proximity to the nerve while reducing the risk of damaging the nerve on implantation. In some embodiments, a device and method is provided comprising at least one nerve detection cannula that detects the nerve and at least one drug delivery cannula to deliver the drug depot near the nerve. In some embodiments, at least one cannula and method is provided that both detects the nerve and delivers the drug depot near the nerve.

FIG. 1 illustrates an embodiment of an "all in one" assembled drug delivery device that both detects the nerve and delivers the drug depot near the nerve. The drug delivery device comprising a cannula 110 and a plunger 130 connected via a housing 125. In various embodiments, the cannula has a proximal end 115 and a distal end having a tip 105 (shown as a beveled tip). The tip at the distal end of the cannula is capable of insertion to a site beneath the skin and the proximal end of the cannula is capable of engaging a housing. Spaced apart from the tip of the cannula 105 is a side port opening 106 that is a sufficient size to allow a drug depot to pass therethrough to the delivery site. Since the spacing between the side port and the tip is known (e.g., 1, 2, 3, 4, 5 mm apart), when the user contacts, for example, the nerve with the tip, the user will know that the side port(s) is 1, 2, 3, 4, 5 mm away from the nerve and can implant the drug depot at a set distance from the nerve. In this way, the blunt tip is used as a probe for the user to manually gauge the distance from the nerve to implant the drug depot. In various embodiments, the proximal end of the cannula is engaged to the housing with a coupling means 120, wherein the coupling means can be a luer lock, threading, friction fit fitting, etc. In some embodiments, the housing has a sensor unit, e.g. a nerve sensing unit 116 that is electrically coupled to an electrical contact (not shown) at the distal end of the cannula to indicate close proximity to a nerve and an alarm 117 to alert the user of close proximity of the tip to the nerve. In various embodiments the sensor unit is electrically coupled, via electrical wire 126, to for example, a power supply, user control switches, a stimulation device, and/or an external monitoring device (exemplary devices not shown). When the tip approaches a nerve or contacts a nerve tissue, the alarm 117 will sound (e.g., buzzer, bell, etc.) or show a visual signal (e.g., light, LED, LCD, etc.) to alert the user that the nerve has been detected.

In some embodiments, the nerve sensing unit may comprise a wire or other electrical conductive material (e.g., metal) running from the tip or distal end of the cannula to a sound and/or visual device that conducts the electrical impulses (e.g., 40 to 90 millivolts (mV)) from the nerve to the sound and/or visual device. In this embodiment, as the user contacts the nerve with the blunt tip of the cannula, the nerve impulse will be conducted through the cannula, through the wire and to the sound and/or visual device, which will alert that user with a visual and/or audio signal that the tip has now contacted a nerve. After the nerve has been detected, the drug depot can be placed in close proximity to the nerve. In this way, deposit of the drug depot in close proximity of the nerve is insured. This placement of the drug depot in close proximity to the nerve allows the therapeutic agent to be released at the target site locally near the nerve. Close proximity to the nerve includes distances that are 1 cm or less. For example, 100 mm, 50 mm, 25 mm, 10 mm, 5 mm, 1 mm, 3 mm or 0.5 mm from the nerve. This local administration of the drug depot near the nerve allows for a lower dose of the therapeutic agent to be used than the usual oral, intravenous, or intramuscular dose. For example, local administration of the drug depot can be accomplished with daily doses that are 20%, 15%, 10%, 5%, 1%, 0.5%, 0.1%, 0.01% of the usual oral, intravenous or intramuscular dose. In turn, systemic side effects, such as for example, liver transaminase elevations, hepatitis, liver failure, myopathy, constipation, etc. may be reduced or eliminated In various embodiments, the drug depot is placed at the target tissue site often using diagnostic imaging procedures, such as for example, X-ray imaging, fluoroscopy, etc. However, often the nerve roots do not show up during the procedure. The devices and methods provided allow the user to detect the nerve with the tip of the cannula or needle and implant the drug depot next to the nerve, where it can provide its local therapeutic effect. In some embodiments, the device comprises one, two, three, four, or five nerve detection cannulas that can be solid or hollow and/or one, two, three, four, or five drug delivery cannulas.

In various embodiments, the cannula is hollow having a sufficient diameter to allow passage of a drug depot and the plunger that facilitates delivery of the drug depot to the designated site beneath the skin. The plunger can have a knob, or gripping features that enable the user to move the plunger in order to deliver the drug depot. The housing may also have grips for the user to hold the housing and connect the cannula to it. The size of the cannula is dictated by the type of drug depot to be delivered and the procedure to be performed.

FIG. 2A illustrates an embodiment of the "all in one" cannula system that detects the nerve and delivers the drug depot near the nerve. Shown in FIG. 2A is an expanded view of the distal end of the cannula shaft 110 of a drug delivery device comprising a tip 105 having a side port 106 for dispensing the drug depot at a delivery site. The distal end of the cannula also has an electrical contact 205 that detects the electrical impulse generated by the nerve when the tip of the cannula 105 contacts the nerve or is in close proximity to the nerve. The electrical contact is electrically coupled via a wire 111 in order to send a signal to the alarm to let the user know that the tip of the cannula contacted or is near the nerve. In this way, the user can move the tip away from the nerve and implant the drug depot near the nerve.

Figure 2B:
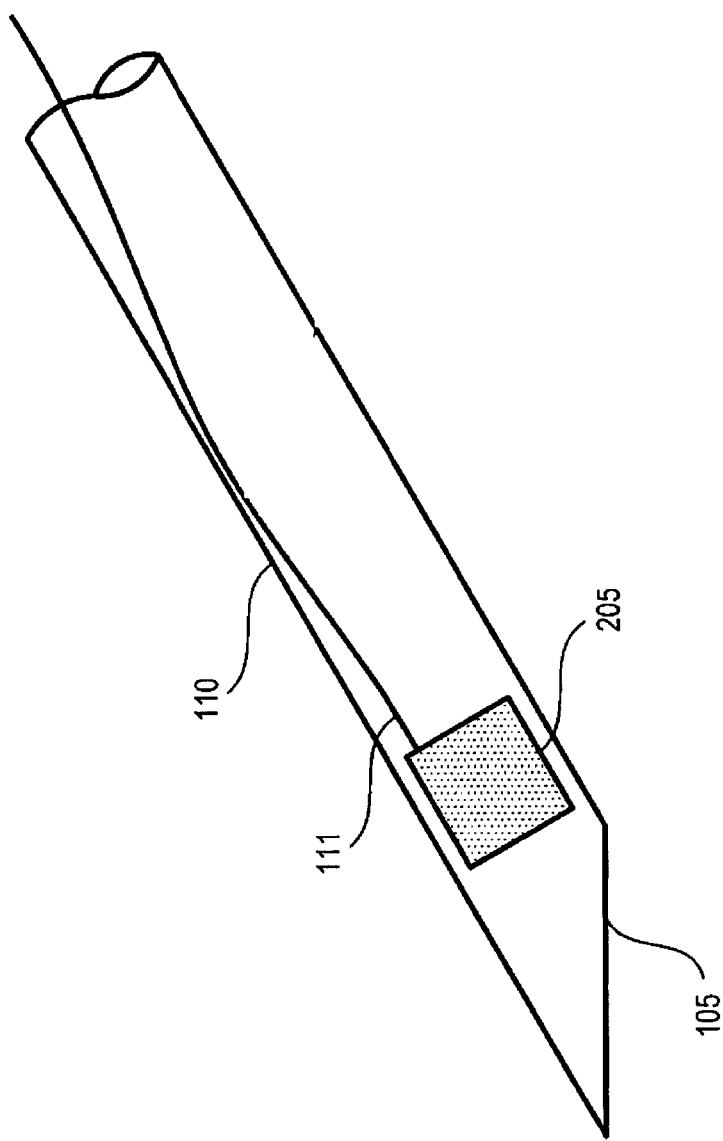
FIG. 2b illustrates an exemplary embodiment of the nerve detection cannula having a sensor to detect proximity to a nerve. This cannula would be part of a two cannula system. One cannula for detecting the nerve (shown) and the other cannula would be for drug delivery (not shown).

FIG. 2B illustrates an embodiment of the nerve detection cannula that can be used with the drug delivery cannula. Shown in FIG. 2B is an expanded view of the distal end of the cannula shaft 110 comprising a tip 105 and the distal end of the cannula also has an electrical contact 205 that detects the electrical impulse generated by the nerve when the tip of the cannula 105 contacts the nerve or is in close proximity to the nerve. The electrical contact is electrically coupled via a wire 111 in order to send a signal to the alarm to let the user know that the tip of the cannula contacted or is near the nerve. In this way, the user can move the tip away from the nerve and implant the drug depot next to the nerve. This cannula can be used with a separate drug delivery cannula (not shown). In some embodiments, the detection cannula detects the nerve and then the drug delivery cannula is inserted next to the nerve and the drug depot delivered to the target site next to the nerve. It will be understood by those of ordinary skill in the art that the nerve detection cannula and the drug delivery cannula can be inserted at the same position (e.g., next to the nerve) or in close proximity to each other (e.g., within 5 cm, 4 cm, 3 cm, 2 cm, 1 cm, 0.5 cm, 10 mm, 5 mm, 1 mm or 0.5 mm). For example, the nerve detection cannula or probe can be placed at or near the nerve and the nerve detected. Next, the nerve detection can be withdrawn and the drug delivery cannula can be positioned in the same position as the nerve detection cannula only near the nerve for delivery of the drug depot. In another embodiment, the nerve detection cannula or probe can be placed at or near the nerve and the nerve detected. Next, the drug delivery cannula can be positioned in close proximity to the nerve detection cannula (e.g., within 5 cm, 4 cm, 3 cm, 2 cm, 1 cm, 0.5 cm, 10 mm, 5 mm, 1 mm or 0.5 mm) and the drug depot delivered near the nerve after the nerve is detected by the nerve detection cannula or probe.

A suitable drug delivery device with cannula for use with the nerve detecting cannula is shown and described in U.S. Ser. No. 11/942,820 filed Nov. 20, 2007 and published as US 20090131908. The entire disclosure is herein incorporated by reference into the present disclosure. When the nerve detection cannula and drug delivery cannula are the same, such as in the all-in-one cannula system, there is no need to withdraw the cannula, as the drug depot can be delivered out of the cannula using the plunger.

Figure 3:
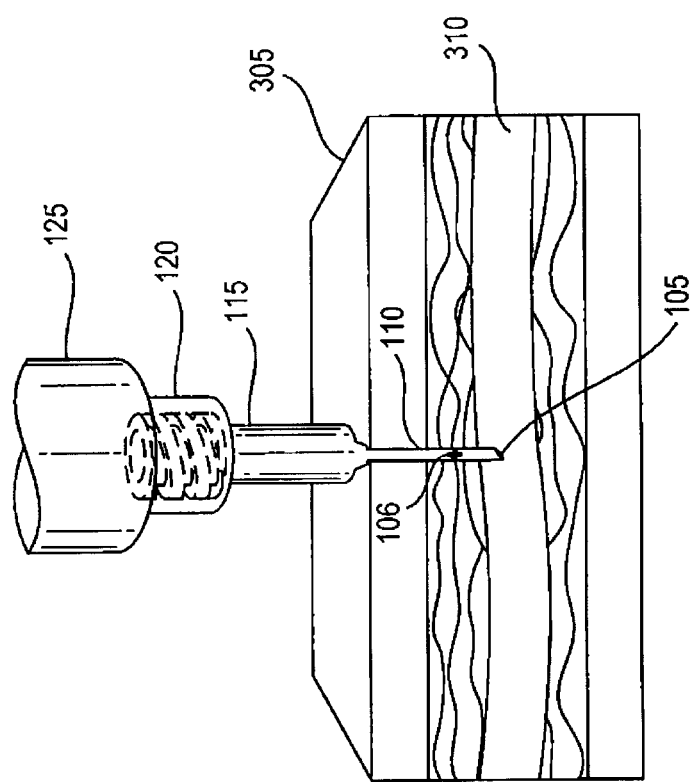
FIG. 3 illustrates an exemplary embodiment of a side sectional view of a drug delivery device inserted at a delivery site beneath the skin, where the device contacts nerve tissue to detect the nerve before implantation of the drug depot next to the nerve.

FIG. 3 illustrates an embodiment of an all in one cannula where the cannula is used for both nerve detection and drug delivery. In this embodiment, a cannula 110 is inserted beneath the skin 305 to deliver the drug depot at a delivery site. The cannula is attached to the housing 125 (shown as a syringe barrel that can store the drug depot in a chamber). The housing can be connected to the cannula by threading or leur fitting 120. In this illustrated embodiment, the tip 105 is contacting a nerve 310. In embodiments, where the sensor is within the housing, the sensor will alert the user via an alarm (not shown) that the blunt tip 105 has contacted the nerve. In some embodiments, the user can monitor the depth of the blunt tip via diagnostic imaging procedures, such as for example, X-ray imaging, fluoroscopy, etc. and know when the nerve is contacted and the distance of the side port opening 106 from the nerve. Thus, the user can implant the drug depot in close proximity to the nerve. In this way, the user can implant the drug depot with precision.

In some embodiments, a device for delivering a drug depot to a delivery site near a nerve of a patient is provided, the device comprising: a first cannula (nerve detection cannula or probe) having a nerve sensing unit comprising an electrical contact and an alarm coupled to the nerve sensing unit, wherein when the cannula contacts the nerve or is in close proximity to the nerve, the alarm is activated to indicate a location of the nerve; a second cannula (drug delivery cannula) having a proximal end and a distal end, the proximal end of the second cannula having an opening to receive the drug depot, the distal end of the second cannula having an opening for passage of the drug depot from the distal end of the second cannula to the delivery site near the nerve of the patient; and a plunger having a handle and a tip adapted for dispensing the drug depot, wherein the tip of the plunger is slidably receivable within the second cannula to deliver the drug depot out the opening of the second cannula to the delivery site near the nerve of the patient.

FIGS. 4-7 illustrate drug delivery cannulas that have a blunt tip that allow the drug depot to be placed as close as possible to the nerve as there is a space between the port opening for drug delivery and the tip of the cannula. These type of cannulas can be used alone or with a nerve detection cannula or probe to deliver the drug depot in close proximity to the nerve.

FIG. 4a illustrates an embodiment of a single barrel cannula (drug delivery cannula) assembly for delivering a drug depot to a single delivery site. This is an example of the drug delivery cannula that is separate from the nerve detection cannula (shown in FIG. 2B). In various embodiments the single barrel cannula assembly comprises a blunt tip 405 at the distal end of the cannula, a side port 410 for dispensing the drug depot at the delivery site, a cannula shaft 415, an index marker 420 to indicate the position of the side port on the cannula shaft and its relative position beneath the skin. The index marker may be located at the proximal end 425 of the cannula assembly and it remains visible to the user during the procedure. The marker 420 will be aligned with and/or parallel to the side port opening so that the user will have a visual indicator of the index marker and can know in what direction the drug depot will be implanted at the delivery site.

FIG. 4b illustrates an embodiment of the top view of the proximal end 425 of a cannula assembly in the drug delivery device. In various embodiments, the proximal end has an opening or chamber 435 configured to receive a drug depot for delivery at a delivery site. In various embodiments, the index marker 420 protrudes from the cannula so that it is visible to the user throughout the procedure. Thus the chamber or channel for the drug depot shown as "a" in 435 will be parallel to the index marker a' and the user will know the position of the chamber and thus the drug depot by looking at the index marker a' of 420. The fitting of the proximal end of the cannula is shown as 425 and is configured to receive a plunger and/or a housing such as a drug cartridge.

FIG. 4c illustrates an embodiment of the cannula shaft 415. In various embodiments, the side port 410, at the distal end of the cannula, is some distance away from the tip of the cannula 405. In various embodiments the distance between the side port and the tip may be between 1-10 mm. In various embodiments the shaft of the cannula is hollow creating a chamber 440 for the passage of the drug depot to the delivery site. In various embodiments, a plunger 445 slides within the cannula and may be used as a guide to slide the drug depot through the cannula shaft and out the side port to the drug delivery site. Again, since the spacing of the side port opening from the blunt tip is known, the user will know the exact distance of implantation from the nerve of the drug depot. Thus, the user can implant the drug depot a set distance from the nerve, which will be beneficial to the patient as the drug can be locally delivered to the area, without injury to the nerve. In FIG. 4c, the plunger is shown in the extended position.

FIG. 4d illustrates a cross-sectional view of an embodiment of a cannula shaft 415, having an inner chamber or channel 440 for passing the drug depot from the proximal end of the cannula to the distal end of the cannula, when the plunger is aligned in the chamber or channel. The passage way for the drug depot is indicated by the "a" and the entrance for the drug depot begins with the chamber or channel marked with an "a" in FIG. 4b. Thus, the entrance of chamber or channel "a" will be aligned from the entrance to the side port opening 415 (shown as an a) and create a passage for the drug depot to be pushed out by the plunger and dispensed at the delivery site. The user will know the position of the drug depot by also viewing the index marker (420a' in FIG. 4b).

FIG. 5a illustrates an embodiment of a double barrel cannula assembly for delivering two drug depots to two delivery sites. In various embodiments, the double barrel cannula assembly comprises a blunt tip 505 at the distal end of the cannula, two side ports 510 for expelling the drug depots at the delivery sites, a cannula shaft 515, an index marker 520, to indicate the position of the side ports beneath the skin. The index marker may be located at the proximal end 525 of the cannula assembly and it remains visible to the user during the procedure. For example, in FIG. 5b, the index marker 520 can be parallel and at a point center to the drug chambers or channels indicated as a and b of 535. The index marker shown as 520b' will be parallel and center to drug chambers or channel 535a and b. By looking at index marker 520b', the user will know the position of the drug chambers or channels a and b. The user will also know the position of the side port openings a and b (shown in of FIG. 5d) and thus will know the angle that the drug depot will be dispensed and the position of the side port openings by viewing index marker 520b'.

FIG. 5b also illustrates an embodiment of the top view of the proximal end 525 of a cannula assembly in the drug delivery device. In various embodiments, the proximal end has two openings or chambers 535a and b, each configured to receive a drug depot for delivery at the delivery sites beneath the skin. In various embodiments, the index marker 520 protrudes from the cannula so that it is visible to the user throughout the procedure. The proximal end of the cannula has a coupling means 525 (e.g., luer fitting, friction fit fitting, threading, etc.) to connect to the housing or to receive a plunger.

FIG. 5c illustrates an embodiment of the cannula shaft 515. In various embodiments, the side ports 510 at the distal end of the cannula are some distance away from the tip of the cannula 505. In various embodiments the distance between the side port and the tip may be from 1, 2, 3, 4, 5, 6, 7, 8, 9, and 10 mm. In various embodiments, the shaft of the cannula is hollow creating two chambers or channels 540(a and b) for the passage of the drug depots to the delivery sites. In various exemplary embodiments, a drug depot is inserted into opening 535, and would travel through the cannula shaft via chamber 540 and would be expelled through side port 510 at a first drug delivery site. In various embodiments, a plunger may be used to facilitate delivery of the drug depot through the cannula shaft and out the side port to the drug delivery site. In various embodiments having two chambers for dispensing two drug depots, the plunger would be appropriately configured to provide two plunging tips 545 that would slide one at a time in each chamber 540 or would simultaneously slide in both chambers because the plungers will have two tips which are in each chamber and dispense the drug depots through each of the side ports. In FIG. 5c, the plunger is shown in the extended position.

FIG. 5d illustrates a cross-sectional view of an embodiment of a cannula shaft 515, having two separate inner chambers 540, wherein each chamber (a and b) corresponds to an opening (a and b of FIG. 5b) at the proximal end for inserting a drug depot as well as a side port 510 at the distal end of the cannula. Each drug depot is contained within its respective chamber, isolated from contact with the adjacent drug depot in the adjacent chamber.

In various embodiments the cannula assembly may be such that the drug delivery sites may vary in position. For example, the drug delivery sites may be adjacent to one another (as illustrated in FIG. 5a), opposite each other (i.e., 180 degree separation), or at a right angle to each other (i.e., 90 degree separation).

FIG. 6a illustrates an embodiment of a triple barrel cannula assembly for delivering three drug depots to three different delivery sites. In various embodiments, the triple barrel cannula assembly comprises a blunt tip 605 at the distal end of the cannula, three side ports (two are shown as 610), each side port can dispense one or more drug depots when the plunger is slid therethrough to different delivery sites. The cannula shaft 615, index markers 620 are aligned with the chambers to indicate the positions of each of the side ports 610 beneath the skin such that the location of each of the three ports beneath the skin is represented by a corresponding index marker 620 located at the proximal end 625 of the cannula assembly visible to the user.

For example, in FIG. 6b, the index marker 620 can be parallel to the drug chambers or channels indicated as a, b, and c of 635. The index marker shown as 620a', b' and c' will be parallel to each drug chamber or channel respectively (shown as 635a, b, and c). By looking at index marker 620a', 620b', and 620c', the user will know the position of the drug chamber or channel 635a, 635b, and 635c, respectively. The user will also know the position of the side port openings a and b (shown in of FIG. 6c) and thus will know the angle that the drug depot will be dispensed and the position of the side port openings by viewing index marker 620.

FIG. 6b also illustrates an embodiment of the top view of the proximal end 625 of a cannula assembly in the drug delivery device. In various embodiments, the proximal end has three openings 635a, b, and c, each configured to receive a drug depot for delivery at the delivery sites beneath the skin. In various embodiments, the three index markers a', b' and c' protruding from the cannula are substantially parallel to each chamber (635a, b, and c) so that they are visible to the user throughout the procedure.

FIG. 6c illustrates an embodiment of the cannula shaft 615. In various embodiments, the side ports 610 (two are shown as a and b, the other is not shown), at the distal end of the cannula, are some distance away from the tip of the cannula 605. In various embodiments, the distance between the side port and the cannula may be between 1-10 mm. In various embodiments, the shaft of the cannula is hollow creating three chambers or channels for the passage of the drug depots to the delivery sites. In various exemplary embodiments, a drug depot inserted into opening 635a of FIG. 6b, would travel through the cannula shaft via the chamber or channel and be dispensed through side port 610a in FIG. 6c at a first drug delivery site. In various embodiments, a plunger may be used to facilitate delivery of the drug depot through the cannula shaft and out the side port to the drug delivery site. In various embodiments having three chambers or channels (a, b, and c in FIG. 6b) for dispensing three drug depots, the plunger would be appropriately configured to provide three plunging tips (not visible) to dispense the drug depots through each of the side ports. In various embodiments, each chamber shaft corresponds to an opening at the proximal end for inserting a drug depot as well as a side port at the distal end of the cannula. Each drug depot is contained within its respective chamber, isolated from contact with adjacent drug depots in adjacent chambers.

FIG. 7a illustrates an embodiment of a quadruple barrel cannula assembly for delivering four drug depots to four delivery sites. In various embodiments the quadruple barrel cannula assembly comprises a tip 705 at the distal end of the cannula, four side ports 710 for expelling four drug depots at the delivery sites, a cannula shaft 715, index markers 720, to indicate the positions of each of the side ports beneath the skin such that the location of each of the four ports beneath the skin is represented by a corresponding index marker located at the proximal end 725 of the cannula assembly visible to the user. Note there are four index markers for a quadruple barrel cannula.

FIG. 7b illustrates an embodiment of the top view of the proximal end 725 of a cannula assembly in the drug delivery device. In various embodiments, the proximal end has four openings or chambers 735 shown as a, b, c, and d, each configured to receive a drug depot for delivery at the delivery sites beneath the skin. In various embodiments, the index markers 720 protrude from the cannula (shown as a', b', c' and d') so that they are visible to the user throughout the procedure. For example, in FIG. 7b, the index marker 720 can be parallel to the drug chambers or channels indicated as a, b, c, and d of 735. The index marker shown as 720a', b', c', and d' will be parallel to each drug chamber or channel respectively (shown as 735a, b, c, and d). By looking at index marker 720a', 720b', and 720c', the user will know the position of the drug chamber or channel 735a, 735b, and 735c, respectively. The user will also know the position of the side port openings (two shown as a and b in FIG. 7c) and thus will know the angle that the drug depot will be dispensed and the position of the side port openings by viewing index marker 720.

FIG. 7c illustrates an embodiment of the cannula shaft 715. In various embodiments, the side ports (two shown as 710a, and b), at the distal end of the cannula, are some distance away from the tip of the cannula 705. In various embodiments the distance between the side port and the tip may be between 1-10 mm. In various embodiments the shaft of the cannula is hollow creating four chambers for the passage of the drug depots to the delivery sites. In various exemplary embodiments, a drug inserted into opening 735 a of FIG. 7B, would travel through the cannula shaft via the first chamber (735a in FIG. 7b) and be dispensed through side port 710a of FIG. 7c at a first drug delivery site. In various embodiments, a plunger may be used to facilitate delivery of the drug depot through the cannula shaft and out the side port to the drug delivery site. In various embodiments having four chambers for dispensing four drug depots, the plunger would be appropriately configured to provide four plunging tips (not visible) to dispel the drug depots in chambers a, b, c, and d of FIG. 7b through each of the side ports. In various embodiments, each chamber shaft corresponds to an opening at the proximal end for inserting a drug depot as well as a side port at the distal end of the cannula. Each drug depot is contained within its respective chamber, isolated from contact with adjacent drug depots in adjacent chambers.

In various embodiments, the cannula assemblies comprising multiple chambers for delivery of one or more drug depots, delivery of the drug depots may be either simultaneous or sequential. In exemplary embodiments, simultaneous delivery may be effected using a plunger configured to engage multiple plunging tips simultaneously. In various embodiments, each plunging tip aligns with an opening at the proximal end of the cannula, corresponding to a chamber in the shaft of the cannula and a side port at the distal end of the cannula. In an exemplary embodiment, when one plunging tip is inserted into an opening, all of the plunging tips are inserted into an opening, such that all plunging tips are slideably received through their respective openings and into their respective chambers in the shaft of the cannula at the same time. The delivery of the drug depot is performed after the nerve is detected.

In various exemplary embodiments where delivery is to be done sequentially, a single plunger having a single plunging tip may be used to dispel the drug depot in one chamber, such that the plunging tip is then slideably removed from the spent chamber and reinserted into a second chamber containing a second drug depot for delivery at a second location beneath the skin. In various embodiments, delivery of a drug depot may be repeated at a single location by reloading the chamber with a subsequent drug depot. In various embodiments, multiple drug doses may be delivered to one or more location without the need to reposition the location of the needle. In some embodiments, the plunger extends out of the cannula shaft to expel the drug depot. In other embodiments, the plunger stays within the cannula shaft but pushes the drug depot out of the cannula.

Various embodiments may employ a housing structure coupled to the proximal end of the cannula suitable for affixing other components to the delivery device. In various embodiments employing a housing structure, the housing structure would be configured such that a plunger inserted through the top of the housing would be properly aligned with the chambers in the cannula to allow drug delivery in the same manner as if the housing were not present. Various embodiments utilizing a housing structure may also employ the use of a drug cartridge configured to connect to the housing such that simultaneous or sequential delivery to one or more drug delivery sites beneath the skin is possible In various embodiments one or more viscous drugs may be delivered simultaneously or sequentially through the chambers of the cannula shaft to one or more drug delivery sites beneath the skin. In various embodiments, a plunger is not need to facilitate delivery of the drug to the deliver site. The cannula shaft may be continuous (single chamber) with multiple distal side ports. In various embodiments one or more viscous drugs may be delivered simultaneously or sequentially through the single chamber of the cannula shaft to multiple sites below the skin.

Cannula or Needle

The cannula or needle of the one or more drug delivery cannulas is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be blunt, beveled, diamond point, ball tip, trocar tip, etc. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks. In various embodiments, the distal end of the cannula has one or more side ports for dispensing a drug depot at a delivery site. In various embodiments, the one or more side ports are located a distance away from the tip. In various embodiments the distance between the tip and the closest edge of the side port may range from 1-10 mm.

The cannula or needle of the drug depot device has a diameter that is larger than the diameter of at least part of the plunger (e.g., tip, middle, etc.) to allow at least part of the plunger to be slidably received within the cannula or needle. In various embodiments, the diameter of the cannula or needle is substantially the same throughout. In other embodiments, the diameter of the needle or cannula becomes smaller approaching the distal end for drug delivery.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. Some examples of lengths of the cannula or needle may include, but are not limited to, from about 50 to 150 mm in length, for example, about 65 mm for epidural pediatric use, about 85 mm for a standard adult and about 150 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 17 to about 25 gauge.

In various embodiments the hollow body of the cannula is divided to form two or more chambers inside the cannula. The dividing walls forming each chamber may be of a similar composition of that of the cannula. Each chamber capable of storing a drug depot. Each chamber has an opening at the proximal end to receive a plunger as well as an opening at the distal end to dispel a drug depot. Multiple chambers of the cannula will allow for the simultaneous passage of one or more drug depots through the cannula to one or more delivery sites without interaction between the drug depots.

In various embodiments, the plunger, cannula or drug depot include markings that indicate location at or near the site beneath the skin. Radiographic markers can be included on the drug depot to permit the user to accurately position the depot into the site of the patient. These radiographic markers will also permit the user to track movement and degradation of the depot at the site over time. In this embodiment, the user may accurately position the depot in the site using any of the numerous diagnostic-imaging procedures. Such diagnostic imaging procedures include, for example, X-ray imaging or fluoroscopy. Examples of such radiographic markers include, but are not limited to, barium, calcium phosphate, and/or metal beads.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

In various embodiments, surrounding the opening of the proximal end of the cannula or needle is a generally cylindrical hub having an engagement means for engaging the housing. Engagement means include, but are not limited to, threading, tracks, clips, ribs, projections, and the like that allow a secure connection between the housing and the proximal end of the cannula. For example, in various embodiments the engagement means may be a luer lock connection, where the cannula has mating threads that mate with the threads disposed on or in the housing.

Housing

The housing may be of various shapes including, but not limited to, cylindrical or round such that the housing allows for the affixation to the cannula as well as the plunger. The housing may also be configured for affixation to other components such as, for example a drug cartridge and an electronic nerve sensing unit.

The housing may comprise a variety of materials, such as, for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof.

Like the cannula or needle, in various embodiments, the housing may have dose indicator markings (e.g., numbers, lines, letters, radiographic markers, etc.) to indicate the number of drug depots delivered. In various embodiments, the plunger includes markings that indicate location at or near the site beneath the skin.

The housing may have contours and allow easy grasping of the device during use. The housing can be angled for right and left hand users or can be generic for both hands. In various embodiments, the housing can comprise an upper opening, a middle opening, and a lower opening. The upper, middle and lower openings allow a plunger to slide through the openings. The middle opening of the housing, in various embodiments, will receive the drug cartridge or the drug depot. In various embodiments, the user can align the drug depot or the chamber of the drug cartridge containing the drug depot with the upper middle and lower openings so that the plunger can pass through and deliver the drug depot.

Plunger

It will be understood that the top end of the plunger may employ a knob, dial, cap, handle or any member that allows the user to utilize the plunger. The plunger has a second end that includes a tip, which is capable of moving the drug depot within the cannula. In other embodiments, the tip of the plunger is sufficiently pointed so that it is capable of insertion to the site beneath the skin of the patient and the cannula or needle is blunted and used to guide the drug depot to the site.

The plunger may be configured to employ multiple tips. The plunger may comprise a single handle having one or more tips attached thereto. The single handle will permit a user to simultaneously insert each of the multiple tips to dispense a drug depot through the cannula. A plunger having multiple tips will best be used in connection with a housing and/or a cannula designed to receive multiple plunger tips for simultaneous distribution of a drug depots. The number of plunger tips will correlate with the chamber design of cannula as well as any housing and drug cartridge that may be used. The each plunger tip is capable of alignment with each of the housing, drug cartridge and cannula chamber that is employed with the delivery of the drug depot.

The plunger has a diameter less than the cannula or needle so that it can be slidably received therein. The plunger may be longer, the same size, or smaller in length than the cannula or needle. In some embodiments, the tip of the plunger can be sharp or blunt.

The plunger may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The plunger may optionally include one or more tapered regions.

Like the cannula or needle, in various embodiments, the plunger may have dose indicator markings (e.g., numbers, lines, letters, radiographic markers, etc.) to indicate the number of drug depots delivered. In various embodiments, the plunger includes markings that indicate location at or near the site beneath the skin.

The plunger tip, which may be a complementary shape to the drug pellet, allows the plunger tip to snuggly fit within the end of the drug pellet for easier drug delivery. The drug pellet may have a rounded end for easier insertion at the desired site. In some embodiments, the tip of the plunger exits the cannula and pushes the drug depot out of the cannula.

Nerve Detection Cannula

The cannula or needle of the nerve detection cannula (or probe) is designed to cause minimal physical and psychological trauma to the patient. Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be blunt, beveled, diamond point, ball tip, trocar tip, etc. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the nerve detection cannula (or probe) or needle, among other things, will depend on the site for nerve detection. For example, the width of the epidural space is only about 3-5 mm for the thoracic region and about 5-7 mm for the lumbar region. Thus, the nerve detection cannula (or probe), in various embodiments, can be designed for these specific areas. Some examples of lengths of the cannula may include, but are not limited to, from about 50 to 150 mm in length, for example, about 65 mm for epidural pediatric use, about 85 mm for a standard adult and about 150 mm for an obese adult patient. The thickness of the cannula will also depend on the site of nerve detection. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 17 to about 25 gauge. The nerve detection cannula or probe comprises some or all of the nerve sensing unit.

Nerve Sensing Unit

In various embodiments, the nerve detection cannula comprises an electronic nerve sensing unit that is incorporated into the drug delivery device (e.g., cannula or needle, housing, etc.). The electronic nerve sensing unit is capable of sensing the presence of a nerve in close proximity to the drug delivery location and alerting the user so the drug depot (e.g., pellet) can be implanted as close as possible to the nerve improving the efficacy of the drug eluting depot. In various embodiments, an electronic device similar to a twitch monitor may be incorporated into the drug delivery device. Suitable nerve sensing units are described in U.S. Pat. Nos. 5,928,158, 5,131,401, and 5,391,081. The entire disclosures of these patents are herein incorporated by reference into the present disclosure.

Other suitable devices include for example, the NIM-ECLIPSE™ Spinal System and NIM-SPINE® System Neural Integrity Monitor (NIM) and nerve monitoring systems disclosed in U.S. Pat. No. 5,196,015, entitled "Procedure for Spinal Pedicle Screw Insertion", and U.S. Pat. No. 5,474,558, entitled "Procedure and System for Spinal Pedicle Screw Insertion" and U.S. Pat. No. 6,554,778, entitled "Biopsy Device with Reuseable Handle." These patent disclosures are also herein incorporated by reference into the present disclosure.

Various embodiments may also include an electronic monitor to track other information measures such as stimulus type, stimulus range, cannula tip sensitivity, amplitude, time, etc.

In some embodiments, the nerve sensing unit (including conductive material, alarms, audio equipment, wires etc.) may be disposed within the housing of the cannula or outside of the housing as long as it allows conduction of the electrical impulse from the nerve site.

In various embodiments, the patient is connected to a Medtronic NIM stimulator and when the device, which is also connected to the NIM circuitry, touches a nerve it closes the circuit and notifies the user with a light and/or audible signal that the needle tip has contacted the nerve. The user now can implant the drug depot at or near to the nerve.

In various embodiments including an electronic nerve sensing unit, the main electronic component of the unit may be incorporated into the housing of the drug delivery device. The electronic sensing unit may incorporate an electrical contact at the distal end of the cannula near the tip. The contact is capable of electronic communication with the nerve sensing unit and is capable of indicating close proximity to a nerve location. Furthermore, in various embodiments, the nerve sensing unit is capable of electronically signaling an alarm device to alert the user of close proximity to a nerve. The alarm may provide audio, visual, or combination notification to the user.

In various embodiments including an electronic nerve sensing unit, the unit may be electronically coupled to any of a variety of devices including a power supply, user control switches, a stimulation device, and/or an external monitoring device. In various embodiments the power supply may e.g., supply power to the alarm feature. In various embodiments the user may control the sensitivity of the contacts using one or more control switches. Further, in various embodiments, the contact is capable of providing a stimulation signal to a location to detect a nerve, detecting a response signal from a nerve, or stimulating a nerve and sensing a response.

For example, electronic stimulation of the nerve can be accomplished by sending 1, 2, 3, 4, 5, 6, 7, 8, 9, 10 mA of current into the nerve and watching for muscle movement. Alternatively, electronic stimulation can be accomplished by sending 1, 2, 3, 4, 5, 6, 7, 8, 9, 10 mA of current into the nerve or region surrounding the nerve. If there is conductivity, then the user knows that he/she is approaching a nerve.

In some embodiments, the nerve sensing unit may comprise a wire or electrical conducting material running from the tip or distal end of the cannula to a sound and/or visual device that conducts the electrical impulses (e.g., 40 to 90 millivolts (mV)) from the nerve to the sound and/or visual device. In this embodiment, as the user contacts the nerve with the tip of the cannula, the nerve impulse will be conducted through the cannula, through the wire and to the sound and/or visual device, which will alert that user with a visual and/or audio signal that the tip has now contacted a nerve. In this way, the drug depot can be placed in close proximity to the nerve improving the efficacy of the drug eluting depot. The plunger now can slide within the cannula and the drug depot can be delivered out the distal end. In this way, the drug depot can be delivered at or close to the nerve. Thus, direct local treatment of the nerve and the tissue surrounding the nerve can be accomplished.

The nerve can include for example, cranial nerves, central nerves, peripheral nerves, and/or autonomic nerves. Some example of nerves include, for example, a spinal cord nerve, a pelvic nerve, a pudendal nerve, a sacral nerve, a peripheral nerve, a sciatic nerve, or the like.

Drug Depot

In various embodiments, the device comprises a drug depot. A drug depot comprises a physical structure to facilitate implantation and retention in a desired site (e.g., a synovial joint, a disc space, a spinal canal, a tissue of the patient, etc.). The drug depot also comprises the drug. The term "drug" as used herein is generally meant to refer to any substance that alters the physiology of the patient. The term "drug" may be used interchangeably herein with the terms "therapeutic agent", "therapeutically effective amount", and "active pharmaceutical ingredient". It will be understood that a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 mm to about 5 cm from the implant site. In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

Examples of drugs suitable for use in the drug depot, include, but are not limited to an anti-inflammatory agent, analgesic agent, or osteoinductive growth factor or a combination thereof. Anti-inflammatory agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof, protein inhibitors of TNF, such as etanercept, Remicade, IL-1, such as Kineret®, p38, RANK, RANKL.

Suitable osteoinductive factors include, but are not limited to, a bone morphogenetic protein, a growth differentiation factor, a LIM mineralization protein or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof. Analgesics also include agents with analgesic properties, such as for example, amitriptyline, carbamazepine, gabapentin, pregabalin, clonidine, or a combination thereof.

A "depot" includes but is not limited to capsules, microspheres, particles, coating, matrices, wafers, pills, pellets or other pharmaceutical delivery compositions. In various embodiments, the depot may comprise a bioerodible, a bioabsorbable, and/or a biodegradable biopolymer that may provide immediate release, or sustained release of the drug. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations. In various embodiments, the drug depot comprises poly(lactide-co-glycolide) (PLGA), polylactide (PLA), polyglycolide (PGA), D-lactide, D,L-lactide, L-lactide, D,L-lactide-ϵ-caprolactone, D,L-lactide-glycolide-ϵ-caprolactone or a combination thereof.

In various embodiments, the drug depot comprises drug pellets loaded with a therapeutically effective amount of the therapeutic agent, wherein the pellets are injected into a synovial joint, a disc space, a spinal canal, or a soft tissue surrounding the spinal canal. In various embodiments, the drug pellets comprise a gel in viscous form and microspheres loaded with a therapeutic agent, wherein the combination of gel and microspheres are positioned into a synovial joint, disc space, a spinal canal, or a soft tissue surrounding the spinal canal of a subject.

A "therapeutically effective amount" is such that when administered, the drug results in alteration of the biological activity, such as, for example, inhibition of inflammation, reduction or alleviation of pain, improvement in the condition, etc. The dosage administered to a patient can be as single or multiple doses depending upon a variety of factors, including the drug's pharmacokinetic properties, the route of administration, patient conditions and characteristics (sex, age, body weight, health, size, etc.), extent of symptoms, concurrent treatments, frequency of treatment and the effect desired.

In one exemplary embodiment, the drug depot is in the form of a pellet. The pellet can be any shape, such as for example, bullet shaped, spherical, substantially spherical, flaked, rod shaped, square, oval, etc. The proximal end of the drug pellet may allow the plunger tip to snuggly fit within the proximal end of the drug pellet for easier drug delivery. The distal end of the drug pellet may be rounded for easier insertion at the site.

In various embodiments, the drug pellet comprises a bullet-shaped body that is made from a biodegradable material. In alternative embodiments, the body of the pellet may be made from a non-biodegradable material. A non-biodegradable body could be a porous hollow chamber filled with the therapeutic agent alone or incorporated into a degradable polymer. It may be desirable to make the body non-degradable to be able to retrieve it after it has released its contents. Non-limiting examples of suitable biodegradable materials for the pellet body include polyorthoesters (POE), polylacticglycolic acid (PLGA) polysacharides (Saber technology), polycapralactone, polyfumarate, tyrosine polycarbonate, etc. The body may be solid, and the therapeutic agent may be dispersed throughout the material that forms the body. The dispersal of the therapeutic agent may be even throughout the body. Alternatively, the concentration of the therapeutic agent may vary throughout the body. As the biodegradable material of the body degrades at the site, the therapeutic agent is released.

Procedures for making pellets include, but are not limited to, extrusion-spheroidization, for spherical pellets where the active pharmaceutical ingredient (API) and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, cylindrical extrudate of uniform shape and size. The size of the opening in the screen or die dictate resultant pellet size. The extrudate is fed onto a rotating disk, which may be smooth or may contain a grid (waffled, grooved, etc.) and the extrudate breaks into small cylinders, which in time are rounded into spherically shaped solids. Subsequently, the pellets are dried to the desired residual moisture content, typically in a fluid bed dryer. Any oversized or undersized product is removed by sieving, and the resulting pellets have a narrow size distribution.

In various embodiments, the API is layered on the solid core of the pellet by solution or suspension layering or powder layering techniques. In solution or suspension layering, an API and any inactive ingredients (excipients, binders, etc.) are suspended or dissolved in water or an organic solvent. The resulting liquid is sprayed onto the outside of a core particle, which may include, for example, non-pareil sugar seed (sugar sphere), microcrystalline cellulose pellets and the like, to make the pellet having the desired potency. Solution or suspension layering may be conducted using a wide variety of process techniques, for example, by fluidized bed, Wurster bottom spray techniques, or the like. When the desired potency has been achieved, pellets are dried to the desired residual moisture content. Any oversized or undersized product may be removed by sieving, and the resulting pellets are narrow in size distribution.

Powder layering may also be used to make the drug pellets. Powdered layering involves the application of a dry powder to the pellet core material. The powder may contain the drug, or may include excipients such as a binder, flow aid, inert filler, and the like. In the powder layering technique a pharmaceutically acceptable liquid, which may be water, organic solvent, with or without a binder and/or excipients, is applied to the core material while applying the dry powder until the desired potency is achieved. When the desired potency has been achieved, the pellets may be seal coated to improve their strength, and are then dried to the desired moisture content. Any oversized or undersized product is removed by sieving, and the resulting pellets are narrow in size distribution.

In one embodiment, the pellet is made using a core of biodegradable material, such as, for example, polyglactin, polylactone, polylactide, etc. The core is then coated with a thin layer of the API, such as an anti-inflammatory agent, analgesic agent, etc. by solution, suspension, or powdered layering until the desired potency is achieved.

In various embodiments, the drug pellets can be different sizes, for example, from about 1 mm to 5 mm in length and have a diameter of from about 0.01 to about 2 mm. The layer or layers will each have a layer thickness of from about 0.005 to 1.0 mm, such as, for example, from 0.05 to 0.75 mm. The drug depot chambers are often larger than the drug depot dimensions to keep the drug depot within the drug chamber.

Like the cannula, needle, or plunger, in various embodiments, the drug depot (e.g., pellet, cartridge, etc.) may have dose indicator markings (e.g., numbers, lines, letters, radiographic markers, etc.) to indicate the number of drug depots delivered. In various embodiments, radiopaque marks are positioned on the depot at opposite ends of the depot to assist in determining the position of the depot relative to the treatment site. For example, the radiopaque marker could be a spherical shape or a ring around the depot.

Drug Cartridge

In various embodiments, the drug depot is stored in a drug cartridge. The drug cartridge comprises one or more chambers, each chamber capable of storing a drug pellet. Each chamber isolates the drug pellet from contact with other drug pellets contained within the cartridge. In this way, overcrowding or multiple pellets in one chamber of the drug cartridge is avoided. Further, drug pellets falling out of the drug cartridge due to limited space in the cartridge is also avoided.

In various embodiments, the drug cartridge is capable of insertion into the housing such that the plunger drug cartridge and the cannula are aligned for delivery of the drug depots. In various embodiments involving simultaneous delivery of multiple drug depots through the cannula, the drug cartridge may be any shape or size that allows for the chambers of the drug cartridge containing the drug depots to be aligned with the chambers of the cannula for delivery of the drug depots to the delivery site. In various embodiments, the drug cartridge is round or linear and is slidably receivable through an opening of the housing such that the cartridge is perpendicular to the housing and to the plunger. To deliver the drug depot, the cartridge is inserted into the housing to align with cannula and plunger. The plunger then slides through the housing and the cartridge forcing the drug depot from the cartridge through the cannula to deliver the drug depot to the target site. In various embodiments, the cartridge comprises superior and inferior covers to contain the drug pellet in the chambers to avoid slippage of the pellets from the cartridge.

In various embodiments, the drug cartridge may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or a combination thereof. In various embodiments, the drug cartridge is not biodegradable.

In some embodiments, the drug cartridge comprises multiple drug chambers, where each chamber comprises one drug depot. In various embodiments the number of chambers will be consistent with the number of chambers in the cannula and the number of drug depots selected for simultaneous delivery.

In various embodiments, the drug depot is secured within a chamber by a superior surface to cover the top of the drug cartridge and an inferior surface to cover the bottom of the drug cartridge. The superior and inferior covers keep the drug depot in place preventing the drug depot from slipping from the cartridge. In various embodiments, the superior and inferior covers are made of a thin layer of material that can be penetrated and can be cored by the plunger and/or depot in order to release the drug depot. In various embodiments the penetrable material may comprise, for example, a bioerodible, a bioabsorbable, and/or a biodegradable biopolymer. Examples of suitable materials include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), mPEG, poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, E-caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), wax, agar, agarose, gel-vitamin or combinations thereof. In various embodiments, the superior and/or inferior covers comprise poly(lactide-co-glycolide) (PLGA), polylactide (PLA), polyglycolide (PGA), D-lactide, D,L-lactide, L-lactide, D,L-lactide-$\epsilon$-caprolactone, D,L-lactide-glycolide-$\epsilon$-caprolactone or a combination thereof.

The drug device components (e.g., cannula or needle, plunger, housing, engagement means, etc.) may be lightweight, disposable and sterilizable such that when the device is assembled (e.g., the drug cartridge is attached to the housing), the weight of the device does not substantially increase. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, the cannula or drug cartridge are pre-loaded with the drug depot. This is advantageous when dealing with multi-dose drug pellets that are relatively small (e.g., 1 mm to 5 mm), the user typically cannot grasp these small pellets and load them into the device. By providing them pre-loaded in a cannula or drug cartridge, the user does not have to substantially manipulate the individual drug pellets and the risk of contaminating the pellets particularly with sterilized pellets is reduced.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot includes a gelatin capsule.

Other methods may also be used to sterilize one or more components of the device, including, but not limited to, gas sterilization, such as, for example, with ethylene oxide or steam sterilization.

In some embodiments, the housing, drug cartridge, and/or cannula are transparent so the user can see the position of the plunger and/or the drug depot in the chamber of the drug cartridge. Thus, indicator markings, in this embodiment, are not needed.

In various embodiments, a kit is provided which may include additional parts along with the drug depot device combined together to be used to implant the drug depot. The kit may include the drug depot device in a first compartment. The second compartment may include the drug cartridge, and any other instruments needed for the implant, such as contact leads for nerve sensing unit. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

In various embodiments, the seal between the plunger tip and the cannula or needle can be air tight so that when the cannula or plunger penetrates the skin, at times, fluid (e.g., blood, spinal fluid, synovial fluid, etc.) may be drawn up into the cannula or needle. This fluid will be expelled when the plunger is re-inserted into the cannula or needle and the drug depot is released.

The device may be used for localized and/or targeted delivery of the drug to a patient to treat a disease or condition such as for example, rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, bone muscles, and the like.

In various embodiments, the drug depot device is used to treat pain, or other diseases or conditions of the patient. Pain includes acute pain and neuropathic pain. Acute pain refers to pain experienced when tissue is being damaged or is damaged (e.g., injury, infection, etc.). As contrasted to acute pain, neuropathic pain serves no beneficial purpose. Neuropathic pain results when pain associated with an injury or infection continues in an area once the injury or infection has resolved. Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area.

Patients include a biological system to which a treatment can be administered. A biological system can include, for example, an individual cell, a set of cells (e.g., a cell culture), an organ, or a tissue. Additionally, the term "patient" can refer to animals, including, without limitation, humans.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized" delivery includes, delivery where one or more drugs are deposited within a tissue, for example, a nerve root of the nervous system or a region of the brain, or in close proximity (within about 10 cm, or preferably within about 5 cm, or about 1 cm for example) thereto. "Targeted delivery system" provides delivery of one or more drugs depots in a quantity of pharmaceutical composition that can be deposited at the target site as needed for treatment of pain, inflammation or other disease or condition.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of delivering a drug depot to a delivery site near a nerve of a patient, the method comprising:
    detecting the nerve of the patient; and
    positioning near the nerve of a patient a cannula having a proximal end and a distal end, the proximal end of the cannula having an opening to receive the drug depot, the distal end of the cannula having a side port containing an opening for passage of the drug depot on a shaft of said distal end of the cannula configured for delivery of said drug depot to the delivery site near the nerve of the patient;
    positioning the side port to deliver said drug depot to the delivery site near the nerve by orientating the position of said side port using an index marker configured to indicate the relative position of said side port when inserted into the skin of a patient; and
    delivering the drug depot at the delivery site near the nerve by sliding a plunger having a handle and a tip adapted for dispensing the drug depot, wherein the tip of the plunger is slidably receivable within the cannula to deliver the drug depot out the side port opening of the cannula to the delivery site near the nerve of the patient and the drug depot being in pellet form and comprising a biodegradable polymer.

2. A method of delivering a drug depot according to claim 1, wherein said detecting the nerve of the patient is performed using a cannula coupled to a nerve sensing unit comprising an electrical contact and an alarm coupled to the nerve sensing unit such that when the cannula is in close proximity to the nerve or contacts the nerve, the alarm is activated.

3. A method of delivering a drug depot according to claim 2, wherein the alarm is audible or visible or audible and visible.

4. A method of delivering a drug depot according to claim 1, wherein the detecting of the nerve of the patient and delivery of the drug depot is performed by the same cannula.

5. A method of delivering a drug depot according to claim 1, wherein the nerve comprises the sciatic nerve.

6. A method of delivering a drug depot according to claim 1, wherein the delivery site near the nerve comprises at least one muscle, ligament, tendon, cartilage, synovial joint, spinal disc, spinal foraminal space, near the spinal nerve root, facet joint or spinal canal.

7. A method of delivering a drug depot according to claim 1, wherein the distal end of the cannula comprises a blunt tip.

8. A method of delivering a drug depot according to claim 1, wherein the drug depot is delivered within 1 cm of the nerve site.

9. A method of delivering a drug depot to a delivery site near a nerve of a patient, the method comprising:
    positioning a first cannula having a nerve sensing unit comprising an electrical contact and an alarm coupled to the nerve sensing unit, wherein the cannula contacts the nerve or is in close proximity to the nerve, the alarm is activated to indicate a location of the nerve;
    positioning near the nerve of the patient a second cannula having a proximal end and a distal end, the proximal end of the second cannula having an opening to receive the drug depot, the distal end of the second cannula having a side port containing an opening for passage of the drug depot on a shaft of said distal end of the second cannula configured for delivery of said drug depot to the delivery site near the nerve of the patient;
    positioning the side port to deliver said drug depot to the delivery site near the nerve by orientating the position of said side port using an index marker configured to indicate the relative position of said side port when inserted into the skin of a patient; and
    delivering the drug depot at the delivery site near the nerve by sliding a plunger having a handle and a tip adapted for dispensing the drug depot, wherein the tip of the plunger is slidably receivable within the second cannula to deliver the drug depot out of the side port opening of the second canal to the delivery site near the nerve of the patient and the drug depot being in pellet form and comprising a biodegradable polymer.

10. A method of delivering a drug depot according to claim 9, wherein the alarm is audible or visible or audible and visible.

11. A method of delivering a drug depot according to claim 9, wherein the nerve comprises the sciatic nerve.

12. A method of delivering a drug depot according to claim 9 wherein the delivery site near the nerve comprises at least one muscle, ligament, tendon, cartilage, synovial joint, spinal disc, spinal foraminal space, near the spinal nerve root, facet joint or spinal canal.

13. A method of delivering a drug depot according to claim 9, wherein the first and second cannulas each comprise a blunt tip.

14. A device for delivering a drug depot at or near a nerve site beneath the skin of a patient, the device comprising: a cannula having a proximal end and a distal end, the proximal end of the cannula having a side port containing an opening to receive the drug depot, the distal end of the cannula capable of insertion at or near the nerve site beneath the skin of the patient and having an opening for passage of the drug depot and an index marker at the proximal end of the cannula, the index marker parallel to and aligned with the opening for passage of the drug depot; a plunger being slidably receivable within the opening of the proximal end of the cannula, the plunger having a first end and a tip at a second end, the first end being capable of moving the tip of the plunger to an extended position; a nerve sensing unit disposed on or within the device, the nerve sensing unit comprising an electrical contact material configured to receive electrical impulses from the nerve site so as to detect the nerve.

15. A device for delivering a drug depot according to claim 14, wherein the electrical contact material is disposed at or in a tip of the distal end of the cannula.

16. A device for delivering a drug depot according to claim 14, wherein the nerve site comprises the sciatic nerve.

17. A device for delivering a drug depot, according to claim 14, wherein the nerve site comprises at least one muscle, ligament, tendon, cartilage, synovial joint, spinal disc, spinal foraminal space, near the spinal nerve root, facet joint or spinal canal.

18. A device for delivering a drug depot to a delivery site near a nerve of a patient, the device comprising:
    a first cannula having a nerve sensing unit comprising an electrical contact and an alarm coupled to the nerve sensing unit, wherein the cannula contacts the nerve or is in close proximity to the nerve, the alarm is activated to indicate a location of the nerve;
    a second cannula having a proximal end and a distal end, the proximal end of the second cannula having a side port containing an opening to receive the drug depot, the distal end of the second cannula having an opening for the passage of the drug depot from the distal end of the second cannula to the delivery site near the nerve of the patient and an index marker at the proximal end of the second cannula, the index marker parallel to and aligned with the opening for passage of the drug depot; and
    a plunger having a handle and a tip adapted for dispensing the drug depot, wherein the tip of the plunger is slidably receivable within the second cannula to deliver the drug depot out of the opening of the second cannula to the delivery site near the nerve of the patient.

19. A device for delivering a drug depot according to claim 18, wherein the electrical contact material is disposed at or in a tip of a distal end of the first cannula and the second cannula is positioned near the first cannula after the nerve is located to deliver the drug depot near the nerve of the patient.

20. A device for delivering a drug depot according to claim 18, wherein the alarm is audible or visible or audible and visible.

* * * * *

UNITED STATES PATENT AND TRADEMARK OFFICE
CERTIFICATE OF CORRECTION

PATENT NO. : 8,715,223 B2  Page 1 of 1
APPLICATION NO. : 12/507197
DATED : May 6, 2014
INVENTOR(S) : McKay It is certified that error appears in the above-identified patent and that said Letters Patent is hereby corrected as shown below:

In the Specification

In Column 7, Line 38, delete "leur" and insert -- luer --, therefor.

In Column 12, Line 22, delete "possible" and insert -- possible. --, therefor.

In Column 19, Line 15, delete "polysacharides" and insert -- polysaccharides --, therefor.

In Column 21, Line 20, delete "E-caprolactone," and insert -- ε-caprolactone, --, therefor.

Signed and Sealed this
Eleventh Day of August, 2015

Michelle K. Lee
*Director of the United States Patent and Trademark Office*